(12) United States Patent
Chang et al.

(10) Patent No.: US 11,630,504 B2
(45) Date of Patent: Apr. 18, 2023

(54) HANDHELD INPUT DEVICE AND ELECTRONIC SYSTEM

(71) Applicant: HTC Corporation, Taoyuan (TW)

(72) Inventors: Wei-Jen Chang, Taoyuan (TW); Fu-Cheng Fan, Taoyuan (TW)

(73) Assignee: HTC Corporation, Taoyuan (TW)

( * ) Notice: Subject to any disclaimer, the term of this patent is extended or adjusted under 35 U.S.C. 154(b) by 0 days.

(21) Appl. No.: 17/412,263

(22) Filed: Aug. 26, 2021

(65) Prior Publication Data

US 2022/0300065 A1 Sep. 22, 2022

Related U.S. Application Data

(60) Provisional application No. 63/161,457, filed on Mar. 16, 2021.

(51) Int. Cl.
*G06F 3/01* (2006.01)
*G06F 3/0354* (2013.01)
(Continued)

(52) U.S. Cl.
CPC .......... *G06F 3/011* (2013.01); *A61B 5/02416* (2013.01); *A61B 5/02438* (2013.01);
(Continued)

(58) Field of Classification Search
CPC .... G06F 3/011; G06F 3/0304; G06F 3/03545; A61B 5/02416; A61B 5/02438; G06T 11/203
See application file for complete search history.

(56) References Cited

U.S. PATENT DOCUMENTS 5,611,036 A * 3/1997 Berend ................. G06T 11/001
　　　　　　　　　　　　　　　　　　　345/441
7,460,111 B2 * 12/2008 Keely ................. G06F 3/03545
　　　　　　　　　　　　　　　　　　　D19/171
(Continued)

FOREIGN PATENT DOCUMENTS

TW　　201804292　　2/2018
TW　　202038056　　10/2020

OTHER PUBLICATIONS

Satake Precision Technology, "ShokacPot STH," accessed Jul. 31, 2021, available at: https://www.satakeps-en.com/items/4922754.
(Continued)

*Primary Examiner* — Benyam Ketema
(74) *Attorney, Agent, or Firm* — JCIPRNET (57) ABSTRACT

The disclosure provides a handheld input device and an electronic system. The handheld input device includes a pen-shaped body, a flexible displacement sensor, and a processor. The flexible displacement sensor is disposed on the pen-shaped body, wherein the flexible displacement sensor deforms in response to a pressing force applied onto the flexible displacement sensor. The processor is coupled to the flexible pressure sensor and disposed in the pen-shaped body, wherein the processor is configured to perform: obtaining a specific displacement of the flexible displacement sensor; determining a stroke size of a representative object in a virtual environment based on the specific displacement of the flexible displacement sensor, wherein the representative object corresponds to the handheld device.

18 Claims, 6 Drawing Sheets

(51) Int. Cl.
*A61B 5/024* (2006.01)
*G06T 11/20* (2006.01)
*G06F 3/03* (2006.01)

(52) U.S. Cl.
CPC ........ *G06F 3/0304* (2013.01); *G06F 3/03545* (2013.01); *G06T 11/203* (2013.01)

(56) References Cited

U.S. PATENT DOCUMENTS

| | | | | |
|---|---|---|---|---|
| 9,740,310 | B2* | 8/2017 | Natzke | G06F 3/04883 |
| 11,209,916 | B1* | 12/2021 | Zimmermann | G06F 3/0325 |
| 11,397,478 | B1* | 7/2022 | Gutierrez | G06F 3/03545 |
| 2008/0180410 | A1* | 7/2008 | McCall | G06T 11/203 |
| | | | | 345/179 |
| 2011/0304643 | A1* | 12/2011 | Marison | G06T 11/40 |
| | | | | 345/611 |
| 2012/0098744 | A1* | 4/2012 | Stinson, III | G06F 3/0304 |
| | | | | 345/158 |
| 2012/0105367 | A1* | 5/2012 | Son | G06F 3/04883 |
| | | | | 345/174 |
| 2013/0009884 | A1* | 1/2013 | Wang | G06F 3/044 |
| | | | | 345/173 |
| 2013/0106766 | A1* | 5/2013 | Yilmaz | G06F 3/0442 |
| | | | | 345/173 |
| 2013/0120426 | A1* | 5/2013 | DiVerdi | G06T 11/001 |
| | | | | 345/589 |
| 2013/0226504 | A1* | 8/2013 | George | G06F 3/03545 |
| | | | | 702/138 |
| 2013/0229360 | A1* | 9/2013 | Liang | G06F 3/04883 |
| | | | | 345/173 |
| 2013/0229389 | A1* | 9/2013 | DiVerdi | G06F 3/0488 |
| | | | | 345/179 |
| 2013/0300694 | A1* | 11/2013 | Guenther | G06F 3/03545 |
| | | | | 345/173 |
| 2014/0198080 | A1* | 7/2014 | Mankowski | G06F 3/03545 |
| | | | | 345/179 |
| 2014/0292690 | A1* | 10/2014 | Sugihara | G06T 11/203 |
| | | | | 345/173 |
| 2015/0153852 | A1* | 6/2015 | DiVerdi | G06F 3/0488 |
| | | | | 345/179 |
| 2016/0342227 | A1* | 11/2016 | Natzke | G06F 3/03545 |
| 2017/0025091 | A1* | 1/2017 | Haddick | G09G 5/02 |
| 2017/0228053 | A1* | 8/2017 | Short | G06F 3/0383 |
| 2018/0024650 | A1* | 1/2018 | Hou | G06F 3/0383 |
| | | | | 345/179 |
| 2018/0188830 | A1* | 7/2018 | Kim | G06F 1/1626 |
| 2019/0094972 | A1 | 3/2019 | Ukita | |
| 2019/0113986 | A1 | 4/2019 | Bikumala et al. | |
| 2019/0377433 | A1* | 12/2019 | Markiewicz | G06F 3/04847 |
| 2020/0033947 | A1* | 1/2020 | Bloom | G06F 3/03545 |
| 2020/0042111 | A1* | 2/2020 | Connellan | G06F 3/04883 |
| 2020/0310561 | A1* | 10/2020 | Connellan | G06F 3/03545 |
| 2020/0383641 | A1* | 12/2020 | Hwang | A61B 5/7278 |
| 2020/0401245 | A1* | 12/2020 | Munakata | G06F 3/0346 |
| 2020/0409532 | A1* | 12/2020 | Murphy | G02B 27/017 |
| 2021/0064153 | A1* | 3/2021 | Yeh | G06F 3/0383 |
| 2021/0103331 | A1* | 4/2021 | Harvey | G06F 3/038 |
| 2021/0200318 | A1* | 7/2021 | Bloom | G06F 3/03545 |
| 2022/0253162 | A1* | 8/2022 | Marshall | G06F 3/0383 |
| 2022/0276729 | A1* | 9/2022 | Gutierrez | G06F 3/016 |
| 2022/0300134 | A1* | 9/2022 | Hori | G06F 3/04162 |

OTHER PUBLICATIONS

"Office Action of Taiwan Counterpart Application", dated Nov. 8, 2022, p. 1-p. 6.

* cited by examiner

HANDHELD INPUT DEVICE AND ELECTRONIC SYSTEM

CROSS REFERENCE TO RELATED APPLICATION

This application claims the priority benefit of U.S. provisional application Ser. No. 63/161,457, filed on Mar. 16, 2021. The entirety of the above-mentioned patent application is hereby incorporated by reference herein and made a part of specification.

BACKGROUND OF THE INVENTION

1. Field of the Invention

The disclosure generally relates to a handheld input device and an electronic system, in particular, to a handheld input device with a flexible displacement sensor and an electronic system.

2. Description of Related Art

Currently, the writing function of a virtual reality (VR) pen may be activated/deactivated by pressing a button on the VR pen. However, the button can only be used to activate/deactivate the writing function, but cannot be used to change the stroke size used for the writing function. That is, when the VR pen is used to write in an VR environment, the size/width of the lines in the handwriting of the VR pen is not adjustable. In this case, it is difficult to create a writhing experience of brush, like a Chinese brush.

SUMMARY OF THE INVENTION

Accordingly, the disclosure is directed to a handheld input device and an electronic system, which may be used to solve the above problems.

The embodiments of the disclosure provide a handheld input device paired with a host device, wherein the handheld input device includes a pen-shaped body, a flexible displacement sensor, and a processor. The flexible displacement sensor is disposed on the pen-shaped body, wherein the flexible displacement sensor deforms in response to a pressing force applied onto the flexible displacement sensor. The processor is coupled to the flexible pressure sensor and disposed in the pen-shaped body, wherein the processor is configured to perform: obtaining a specific displacement of the flexible displacement sensor; determining a stroke size of a representative object in a virtual environment based on the specific displacement of the flexible displacement sensor, wherein the representative object corresponds to the handheld device.

The embodiments of the disclosure provide an electronic system including a handheld input device and a host device. The handheld input device includes a flexible displacement sensor deforming in response to a pressing force. The host device is paired with the handheld input device and provides a virtual environment. The handheld input device obtains a specific displacement of the flexible displacement sensor and provides the specific displacement of the flexible displacement sensor to the host device. The host device determines a stroke size of a representative object in the virtual environment based on the specific displacement of the flexible displacement sensor, wherein the representative object corresponds to the handheld device.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Reference will now be made in detail to the present preferred embodiments of the invention, examples of which are illustrated in the accompanying drawings. Wherever possible, the same reference numbers are used in the drawings and the description to refer to the same or like parts.

Figure 1:
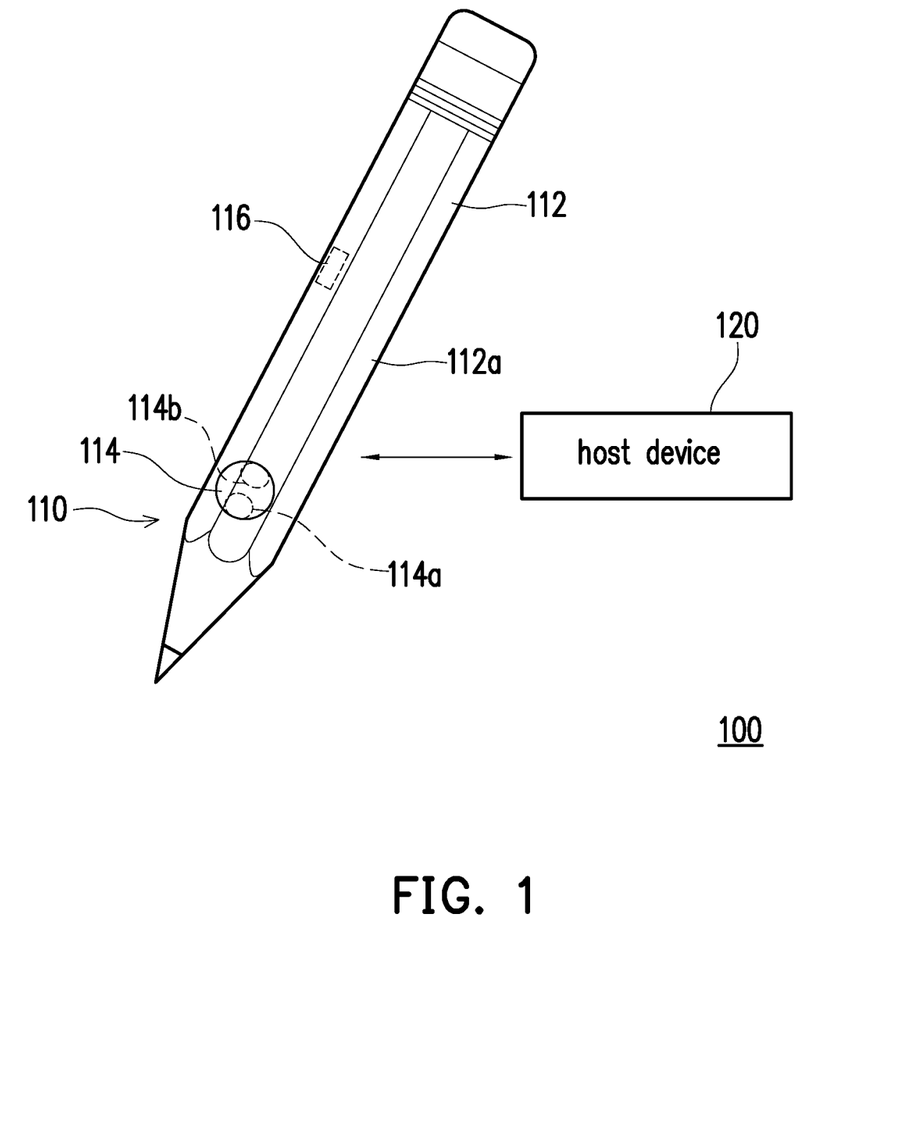
FIG. 1 shows a schematic diagram illustrating an electronic system according to an embodiment of the disclosure.

FIG. 1 shows a schematic diagram illustrating an electronic system according to an embodiment of the disclosure. In FIG. 1, the electronic system 100 includes a handheld input device 110 and a host device 120 paired with the handheld input device 110. In various embodiments, the electronic system 100 may be a VR system, wherein the host device 120 may be used to provide VR services to the user of the VR system. For example, the host device 120 may be a computer device that runs a VR program and may be used to generate VR contents for the user to see. In some embodiments, the VR system may further include a head-mounted display (HMD), and the host device 120 may provide the VR contents to the HMD for the user wearing the HMD to see. In other embodiments, the host device 120 may be a standalone HMD which runs the VR program and generates VR contents for the user wearing the host device 120 to see, but the disclosure is not limited thereto. In other embodiments, the VR system may include other elements such as handheld controllers, movement tracking elements, etc.

In one embodiment, the handheld input device 110 may be understood as a VR pen that can be used by the user to write in a VR environment provided by the host device 120.

In FIG. 1, the handheld input device 110 includes a pen-shaped body 112, a flexible displacement sensor 114, and a processor 116. The pen-shaped body 112 has a holding portion 112a that can be held by the hand of the user. The flexible displacement sensor 114 is disposed on the holding portion 112a, wherein the flexible displacement sensor 114 may be deformed in response to a pressing force applied onto the flexible displacement sensor 114.

The processor 116 is coupled to the flexible pressure sensor 114 and disposed in the pen-shaped body 112. In various embodiments, the processor 116 may be a processor for general purposes, a processor for special purposes, a conventional processor, a digital signal processor, a plurality of microprocessors, one or more microprocessors, controllers and microcontrollers which are combined with a core of the digital signal processor, an application specific integrated circuit (ASIC), a field programmable gate array (FPGA), any other integrated circuits, a state machine, a processor based on advanced RISC machine (ARM) and the like.

In the embodiments of the disclosure, the processor 116 is configured to perform: obtaining a specific displacement of the flexible displacement sensor 114; determining a stroke size of a representative object in the virtual environment (e.g., the VR environment) based on the specific displacement of the flexible displacement sensor 114, wherein the representative object corresponds to the handheld input device 110. Detailed discussion would be provided in the following.

Figure 2:
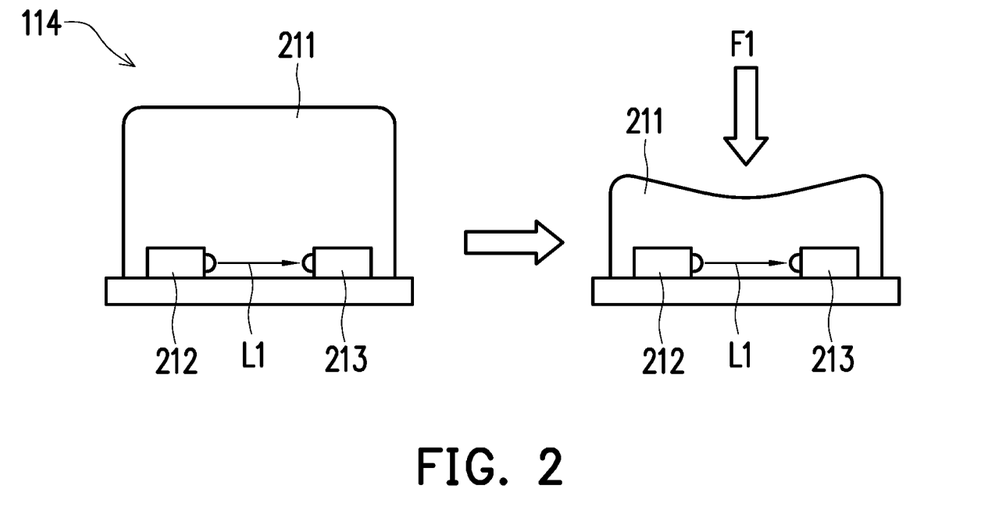
FIG. 2 shows a structural diagram of the flexible displacement sensor according to an embodiment of the disclosure.

See FIG. 2, which shows a structural diagram of the flexible displacement sensor according to an embodiment of the disclosure. In FIG. 2, the flexible displacement sensor 114 includes a deformable body 211, a light emitter 212, and a photodetector 213. In some embodiments, the deformable body 211 may be made of any material that can be deformed when receiving a pressing force F1, such as a foam and/or a sponge, wherein the pressing force F1 may be applied by the finger, e.g., the thumb, of the user holding the handheld input device 110.

The light emitter 212 is disposed in the deformable body 211 and emits a light L1. The photodetector 213 is disposed in the deformable body 211 and receives the light L1. In some embodiments, in response to the pressing force F1, the deformable body 211 is deformed to partially block a light path of the light L1 because the transmittance is decreased by increasing of the density of the deformable body 21, and correspondingly reduces a light intensity of the light L1 detected by the photodetector 213. That is, when the deformable body 211 receives the pressing force F1, the photodetector 213 may correspondingly detect a reduced light intensity of the light L1. Accordingly, the processor 116 determines the specific displacement of the flexible displacement sensor 114 based on the light intensity of the light L1.

In some embodiments, the specific displacement of the flexible displacement sensor 114 is negatively related to the light intensity of the light L1. That is, the lower the light intensity of the light L1, the higher the specific displacement, and vice versa. In some embodiments, the corresponding relationship between the light intensity of the light L1 and the specific displacement of the flexible displacement sensor 114 may be defined in advance. Therefore, when the processor 116 receives the light intensity of the light L1 from the photodetector 213, the processor 116 may accordingly obtain the specific displacement of the flexible displacement sensor 114.

In some embodiments, the processor 116 determines the stroke size of the representative object in the virtual environment based on the specific displacement of the flexible displacement sensor 114.

Figure 3:
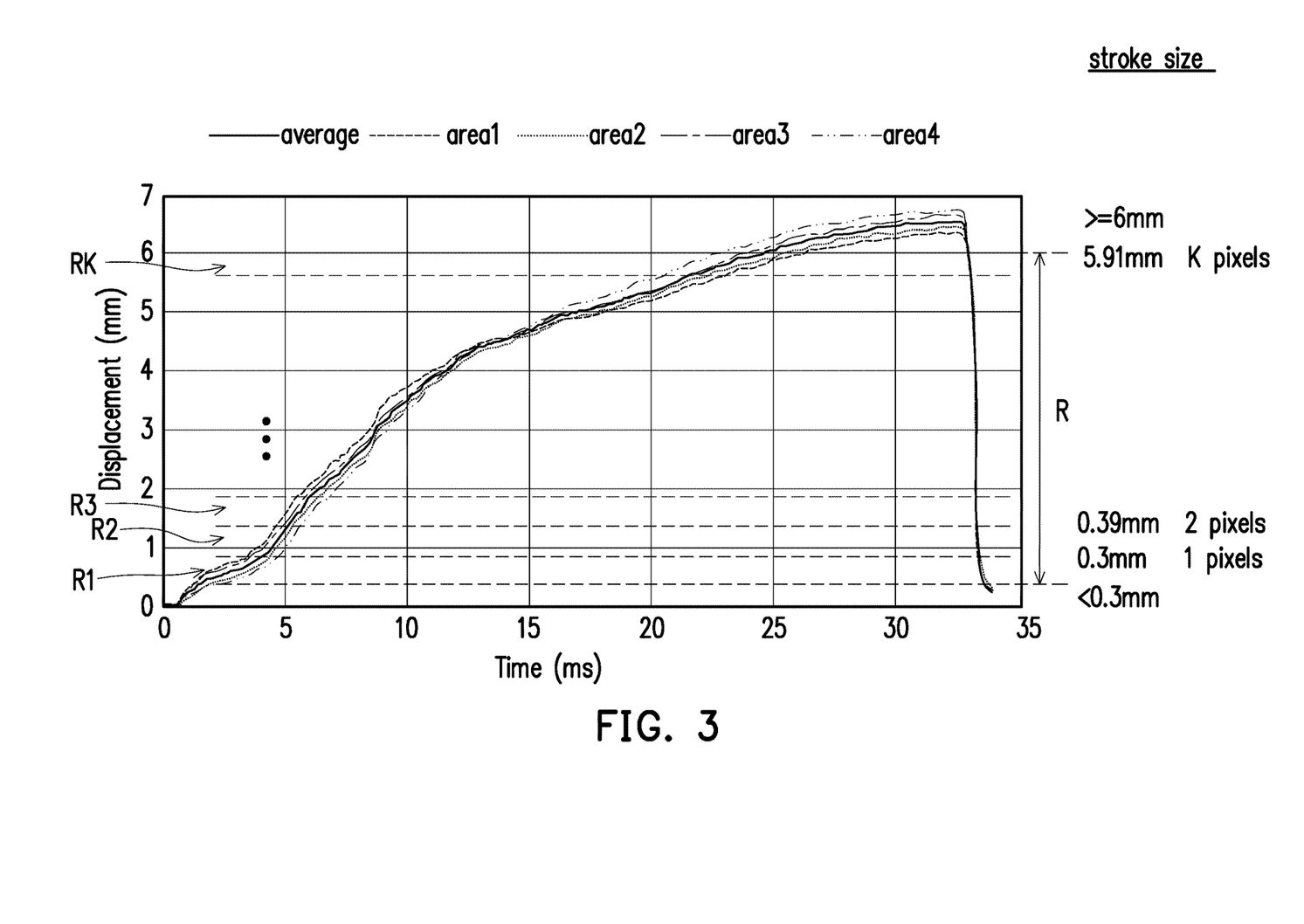
FIG. 3 shows a schematic diagram of determining the stroke size based on the specific displacement of the flexible displacement sensor according to an embodiment of the disclosure.

See FIG. 3, which shows a schematic diagram of determining the stroke size based on the specific displacement of the flexible displacement sensor according to an embodiment of the disclosure. In FIG. 3, the pressing force F1 is increased along with the time. In some embodiments, the flexible displacement sensor 114 may be divided into sensing area 1 to sensing area 4, and the processor 116 may obtain the displacement of each of the sensing areas 1 to 4 and accordingly obtain the average displacement of the sensing areas 1 to 4 as the specific displacement of the flexible displacement sensor 114, which is illustrated as the solid line in FIG. 3.

In one embodiment, the stroke size of the representative object may be one of a plurality of predetermined stroke sizes. In FIG. 3, the predetermined stroke sizes may include 1 pixel to K pixels (K is an integer), but the disclosure is not limited thereto.

In one embodiment, the K predetermined stroke sizes may respectively correspond to a plurality of sub-ranges R1-RK in a predetermined displacement range R. For example, the sub-range R1 corresponding to the predetermined stroke size of 1 pixel may range from 0.3 mm to 0.39 mm; the sub-range RK corresponding to the predetermined stroke size of K pixels may range from 5.91 mm to 6 mm, but the disclosure is not limited thereto.

In one embodiment, the processor 116 may find, from the sub-ranges R1-RK, a first sub-range to which the specific displacement belongs. For example, if the specific displacement of the flexible displacement sensor 114 is 0.33 mm, the processor 116 may find the sub-range R1 to which the specific displacement belongs as the first sub-range; if the specific displacement of the flexible displacement sensor 114 is 5.93 mm, the processor 116 may find the sub-range RK to which the specific displacement belongs as the first sub-range, but the disclosure is not limited thereto.

Next, the processor 116 may find, from the predetermined stroke sizes, a first predetermined stroke size corresponding to the first sub-range as the stroke size of the representative object in the virtual environment. For example, if the first sub-range is determined to be the sub-range R1, the processor 116 may accordingly determine 1 pixel as the stroke size of the representative object; if the first sub-range is determined to be the sub-range RK, the processor 116 may accordingly determine K pixels as the stroke size of the representative object.

In some embodiments, in response to the processor 116 determining that the specific displacement of the flexible displacement sensor 114 belongs to a range higher than the highest sub-range RK in the predetermined displacement range R, the processor 116 may determine the largest predetermined stroke size (e.g., K pixels) as the stroke size of the representative object.

In some embodiments, in response to the processor 116 determining that the specific displacement of the flexible displacement sensor 114 belongs to a range lower than the lowest sub-range R1 in the predetermined displacement range R, the processor 116 may ignore the specific displacement of the flexible displacement sensor 114. That is, the processor 116 may determine that the flexible displacement sensor 114 is not receiving any pressing force.

As mentioned in the above, the flexible displacement sensor 114 may be divided into multiple sensing areas. In some embodiments, the user may press any of the sensing areas on the flexible displacement sensor 114 to activate corresponding function of the handheld input device 110. For example, in FIG. 1, the flexible displacement sensor 114 may include sensing areas 114a and 114b, wherein the sensing area 114a may be closer to the tip of the pen-shaped body 112 than the sensing area 114b. In one embodiment, in response to determining that the pressing force F1 is applied onto the sensing area 114a, the processor 116 may determine that the representative object corresponding to the handheld input device 110 is used to provide a writing function in the virtual environment.

In some embodiments, the processor 116 may obtain a moving track of the handheld input device 110 and provide the moving track of the handheld input device 110 to the host device 120. Accordingly, the host device 120 may combine the moving track of the handheld input device 110 with the stroke size of the representative object to create a stroke track of the representative object in the virtual environment. That is, when the user moves the handheld input device 110, the representative object would be correspondingly moved to write with the determined stroke size in the virtual environment.

On the other hand, in response to determining that the pressing force F1 is applied onto the sensing area 114b, the processor 116 may determine that the representative object corresponding to the handheld input device 110 is used to provide an erasing function in the virtual environment. That is, when the user moves the handheld input device 110, the representative object with the determined stroke size would be correspondingly moved to erase with the determined stroke size in the virtual environment, but the disclosure is not limited thereto.

In some embodiments, the processor 116 may perform other detections with the flexible displacement sensor 114.

Figure 4:
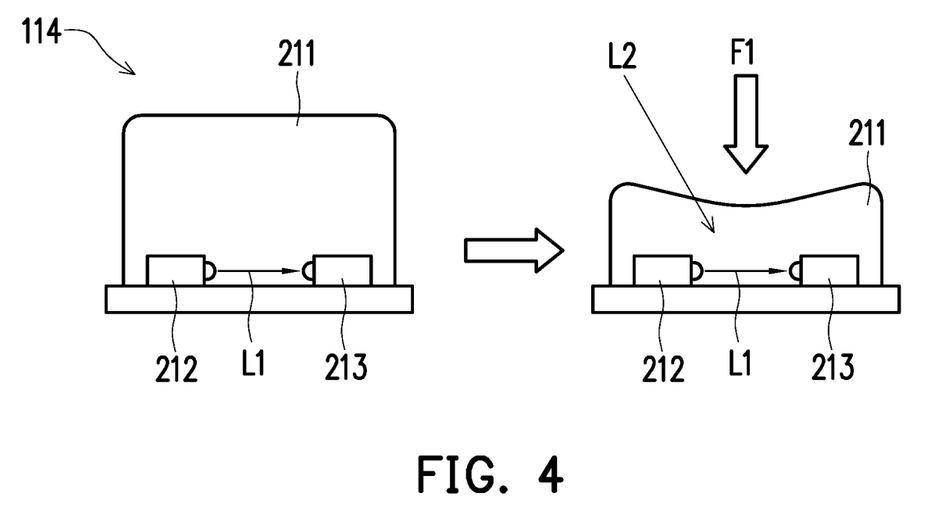
FIG. 4 shows a schematic diagram of the flexible displacement sensor receiving an external light according to an embodiment of the disclosure.

See FIG. 4, which shows a schematic diagram of the flexible displacement sensor receiving an external light according to an embodiment of the disclosure. In FIG. 4, the deformable body 211 may be made of a semi-transparent material that allows an external light L2 outside of the deformable body 211 to be received by the photodetector 213. In this case, the photodetector 213 may detect a combined light intensity of the light L1 and the external light L2. In one embodiment, the variation of the combined light intensity of the light L1 and the external light L2 may include a direct component and an alternating component. In the embodiment, the processor 116 may determine the specific displacement of the flexible displacement sensor 114 based on the direct component of the variation of the combined light intensity of the light L1 and the external light L2.

In addition, since the blood flow at the user's finger varies in response to the heart rate of the user, when the user touches the deformable body 211 with the user's finger, the light intensity of the external light L2 would vary in response to the blood flow of the user, which leads to the alternating component of the variation of the combined light intensity. Therefore, the processor 116 may further determine the heart rate of the user touching the deformable body 211 based on the alternating component of the variation of the combined light intensity of the light L1 and the external light L2.

In some embodiments, the handheld input device of the disclosure may be used to scan the outline of physical object with specifically designed flexible displacement sensor.

Figure 5:
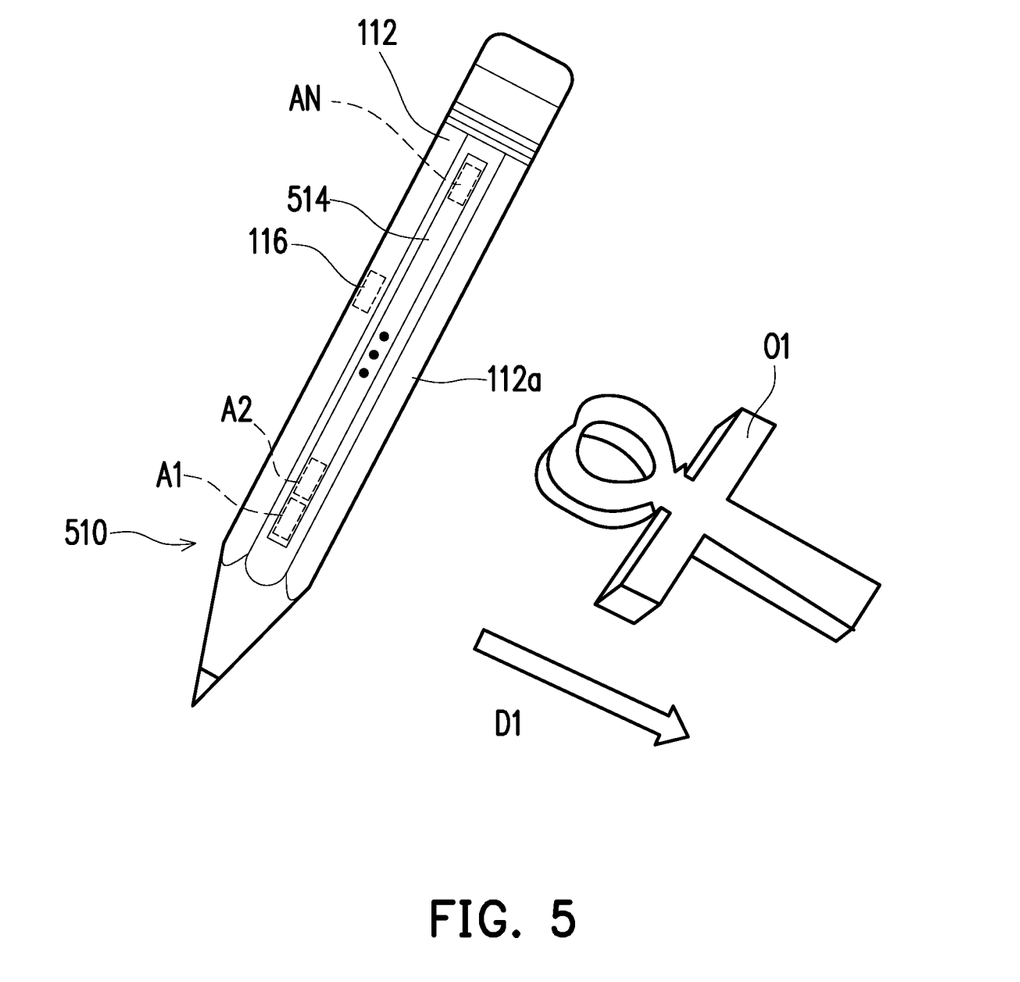
FIG. 5 shows a schematic diagram of the handheld input device according to an embodiment of the disclosure.

See FIG. 5, which shows a schematic diagram of the handheld input device according to an embodiment of the disclosure. In FIG. 5, the handheld input device 510 includes the pen-shaped body 112, a flexible displacement sensor 514, and the processor 116. The pen-shaped body 112 has the holding portion 112a that can be held by the hand of the user. The flexible displacement sensor 514 is disposed on the holding portion 112a, wherein the flexible displacement sensor 514 may be deformed in response to a pressing force applied onto the flexible displacement sensor 514.

In the embodiment, the flexible displacement sensor 514 is bar-shaped and has a plurality of sensing areas A1-AN. In one embodiment, the handheld input device 510 may be switched to operate in a scan mode. In this case, the processor 116 may obtain a moving track of the handheld input device 116 and obtain a displacement of each of the sensing areas A1-AN.

In FIG. 5, assuming that the handheld input device 510 is moved along the direction D1, and the sensing areas A1-AN are used to touch the surface of the physical object O1 during the movement of the handheld input device 510. In this case, the displacement of each of the sensing areas A1-AN would vary in response to the outline of the physical object O1 during the movement of the handheld input device 510. Therefore, the processor 116 may determine the outline of the physical object O1 touched by the flexible displacement sensor 514 based on the moving track of the handheld input device 510 and the displacement of each of the sensing areas A1-AN. That is, the handheld input device 510 may be used to scan the outline of the physical object O1.

In one embodiment, the processor 116 may further provide the outline of the physical object O1 to the host device 120. Accordingly, the host device 120 may create a virtual object corresponding to the physical object O1 in the virtual environment based on the outline of the physical object O1.

Figure 6:
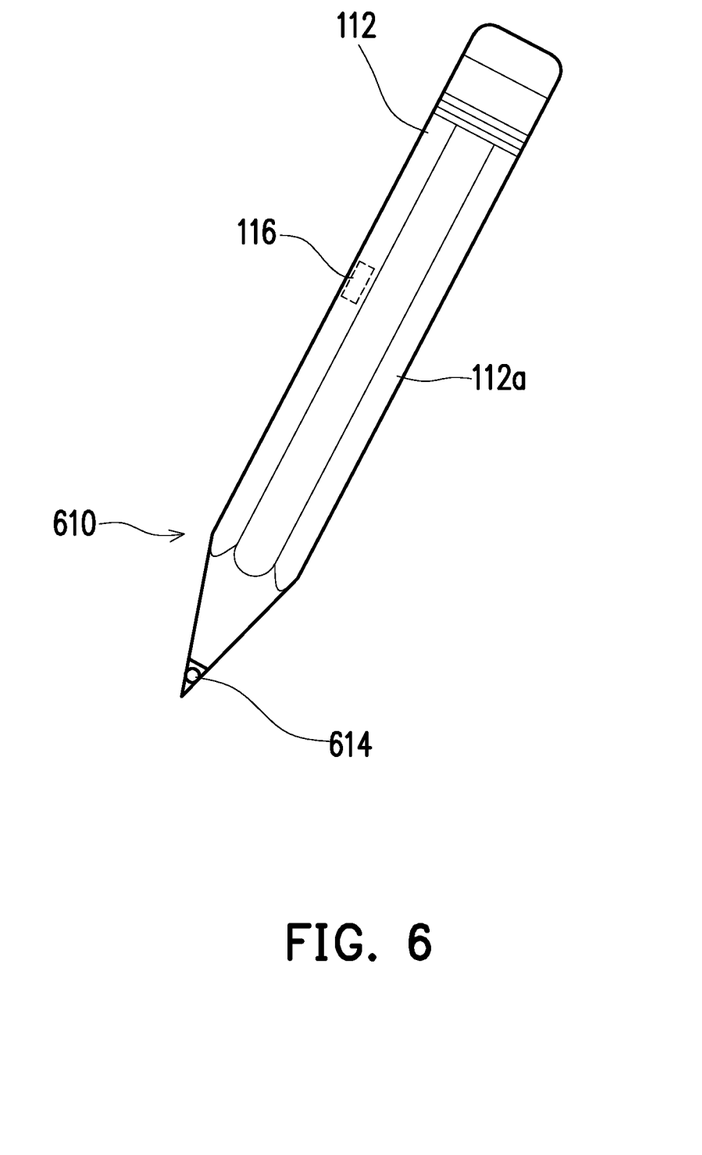
FIG. 6 shows a schematic diagram of the handheld input device according to an embodiment of the disclosure.

See FIG. 6, which shows a schematic diagram of the handheld input device according to an embodiment of the disclosure. In FIG. 6, the handheld input device 610 includes the pen-shaped body 112, a flexible displacement sensor 614, and the processor 116. The pen-shaped body 112 has the holding portion 112a that can be held by the hand of the user. The flexible displacement sensor 614 is disposed on the tip of the pen-shaped body 112, wherein the flexible displacement sensor 614 may be deformed in response to a pressing force applied onto the flexible displacement sensor 614.

In the embodiment, the user may use the handheld input device 610 as a regular pen to write on some physical surfaces (e.g., a desk), such that the flexible displacement sensor 614 would receive pressing forces from the touched surface during the user writing. In this case, when the user writes with higher force, the stroke size of the representative object corresponding to the handheld input device 610 in the virtual environment would be larger due to the flexible displacement sensor 614 has received higher force, and vice versa.

In some embodiments, the host device 120 may create a virtual object having a surface corresponding to the physical surface in the virtual environment. In this case, when the user uses the handheld input device 610 to write on the physical surface, the host device 120 may accordingly create a stroke track on the surface on virtual object in the virtual environment, but the disclosure is not limited thereto.

In other embodiments, the handheld input devices in the above embodiments may simply be used to obtain the specific displacement of the corresponding flexible displacement sensor and provide the specific displacement to the host device 120. Accordingly, the host device 120 may perform subsequent operations, such as determining the stroke size of the representative object, the heart rate of the user, the stroke track, the outline of the scanned physical object, etc, and the details of these operations may be referred to the above embodiments, which would not be repeated herein.

In summary, the flexible displacement sensor on the handheld input device may provide a specific displacement in response to the pressing force applied onto the flexible displacement sensor, and the specific displacement may be used to determine the stroke size of the representative object corresponding to the handheld input device. Therefore, the handheld input device allows the user to choose the required stroke size by changing the pressing force applied onto the flexible displacement sensor, which provides a novel input experience in the virtual environment. For example, when the user writes/draws a line in the virtual environment, the user may adjust the pressing force applied onto the flexible displacement sensor during writing/drawing the line, such that the width of the line would not be same. Accordingly, the user may have a writhing experience of using a brush (e.g., a Chinese brush) to write in the virtual environment.

It will be apparent to those skilled in the art that various modifications and variations can be made to the structure of the disclosure without departing from the scope or spirit of the invention. In view of the foregoing, it is intended that the disclosure cover modifications and variations of this invention provided they fall within the scope of the following claims and their equivalents.

What is claimed is:

1. A handheld input device, paired with a host device, comprising:
   a pen-shaped body;
   a flexible displacement sensor, disposed on the pen-shaped body, wherein the flexible displacement sensor deforms in response to a pressing force applied onto the flexible displacement sensor, the flexible displacement sensor is bar-shaped and has a plurality of sensing areas;
   a processor, coupled to the flexible pressure sensor and disposed in the pen-shaped body, wherein the processor is configured to perform:
      obtaining a specific displacement of the flexible displacement sensor;
      determining a stroke size of a representative object in a virtual environment based on the specific displacement of the flexible displacement sensor, wherein the representative object corresponds to the handheld input device;
      in response to determining that the handheld input device is operating in a scan mode, obtaining a moving track of the handheld input device and obtaining a displacement of each of the sensing areas;
      determining an outline of a physical object touched by the flexible displacement sensor based on the moving track of the handheld input device and the displacement of each of the sensing areas.

2. The handheld input device according to claim 1, wherein the flexible displacement sensor comprises:
   a deformable body, receiving the pressing force;
   a light emitter, disposed in the deformable body and emitting a light;
   a photodetector, disposed in the deformable body and receiving the light, wherein in response to the pressing force, the deformable body is deformed to partially block a light path of the light and correspondingly reduce a light intensity of the light.

3. The handheld input device according to claim 2, wherein the processor determines the specific displacement of the flexible displacement sensor based on the light intensity of the light.

4. The handheld input device according to claim 2, wherein the deformable body is semi-transparent and allows the photodetector to further receive an external light outside of the deformable body, wherein a variation of a combined light intensity of the light and the external light comprises a direct component and an alternating component, and the processor determines the specific displacement of the flexible displacement sensor based on the direct component of the variation of the combined light intensity of the light and the external light.

5. The handheld input device according to claim 4, wherein the processor determines a heart rate based on the alternating component of the variation of the combined light intensity of the light and the external light.

6. The handheld input device according to claim 1, wherein the stroke size is one of a plurality of predetermined stroke sizes, the predetermined stroke sizes respectively correspond to a plurality sub-ranges in a predetermined displacement range, and the processor is configured to perform:
   finding, from the sub-ranges, a first sub-range to which the specific displacement belongs;
   finding, from the predetermined stroke sizes, a first predetermined stroke size corresponding to the first sub-range as the stroke size of the representative object in the virtual environment.

7. The handheld input device according to claim 1, wherein the flexible displacement sensor has a first sensing area and a second sensing area, and the processor is configured to perform:
   in response to determining that the pressing force is applied onto the first sensing area, determining that the representative object corresponding to the handheld input device is used to provide a writing function in the virtual environment;
   in response to determining that the pressing force is applied onto the second sensing area, determining that the representative object corresponding to the handheld input device is used to provide an erasing function in the virtual environment.

8. The handheld input device according to claim 1, wherein the processor is further configured to perform:
   obtaining the moving track of the handheld input device;
   providing the moving track of the handheld input device to the host device, wherein the host device combines the moving track of the handheld input device with the stroke size of the representative object and accordingly creates a stroke track of the representative object in the virtual environment.

9. The handheld input device according to claim 1, wherein the processor is further configured to perform:
   providing the outline of the physical object to the host device, wherein the host device creates a virtual object corresponding to the physical object in the virtual environment.

10. An electronic system, comprising:
    a handheld input device, comprising a flexible displacement sensor deforming in response to a pressing force, wherein the flexible displacement sensor is bar-shaped and has a plurality of sensing areas;
    a host device, paired with the handheld input device and provides a virtual environment,
    wherein the handheld input device obtains a specific displacement of the flexible displacement sensor and provides the specific displacement of the flexible displacement sensor to the host device;
    wherein the host device determines a stroke size of a representative object in the virtual environment based on the specific displacement of the flexible displacement sensor, wherein the representative object corresponds to the handheld input device;
    wherein the host device is configured to perform:
      in response to determining that the handheld input device is operating in a scan mode, obtaining a moving track of the handheld input device and obtaining a displacement of each of the sensing areas;

providing the displacement of each of the sensing areas to the host device, wherein the host device determines an outline of a physical object touched by the flexible displacement sensor based on the moving track of the handheld input device and the displacement of each of the sensing areas.

11. The electronic system according to claim 10, wherein the flexible displacement sensor comprises:
 a deformable body, receiving the pressing force applied onto the flexible displacement sensor;
 a light emitter, disposed in the deformable body and emitting a light;
 a photodetector, disposed in the deformable body and receiving the light, wherein in response to the pressing force, the deformable body is deformed to partially block a light path of the light and correspondingly reduce a light intensity of the light.

12. The electronic system according to claim 11, wherein the handheld input device determines the specific displacement of the flexible displacement sensor based on the light intensity of the light.

13. The electronic system according to claim 11, wherein the deformable body is semi-transparent and allows the photodetector to further receive an external light outside of the deformable body, wherein a variation of a combined light intensity of the light and the external light comprises a direct component and an alternating component, and the handheld input device determines the specific displacement of the flexible displacement sensor based on the direct component of the variation of the combined light intensity of the light and the external light.

14. The electronic system according to claim 13, wherein the handheld input device determines a heart rate based on the alternating component of the variation of the combined light intensity of the light and the external light.

15. The electronic system according to claim 10, wherein the stroke size is one of a plurality of predetermined stroke sizes, the predetermined stroke sizes respectively correspond to a plurality sub-ranges in a predetermined displacement range, and the host device is configured to perform:
 finding, from the sub-ranges, a first sub-range to which the specific displacement belongs;
 finding, from the predetermined stroke sizes, a first predetermined stroke size corresponding to the first sub-range as the stroke size of the representative object in the virtual environment.

16. The electronic system according to claim 10, wherein the flexible displacement sensor has a first sensing area and a second sensing area, and the handheld input device is configured to perform:
 in response to determining that the pressing force is applied onto the first sensing area, determining that the representative object corresponding to the handheld input device is used to provide a writing function in the virtual environment;
 in response to determining that the pressing force is applied onto the second sensing area, determining that the representative object corresponding to the handheld input device is used to provide an erasing function in the virtual environment.

17. The electronic system according to claim 10, wherein the handheld input device is further configured to perform:
 obtaining the moving track of the handheld input device;
 providing the moving track of the handheld input device to the host device, wherein the host device combines the moving track of the handheld input device with the stroke size of the representative object and accordingly creates a stroke track of the representative object in the virtual environment.

18. The electronic system according to claim 11, wherein the host device is further configured to perform:
 creating a virtual object corresponding to the physical object in the virtual environment.

* * * * *